United States Patent [19]

Miller

[11] 4,161,600

[45] Jul. 17, 1979

[54] DEXTRO AND LEVO-6-OXO-2-PIPERIDINECARBOXYLIC ACID QUININE SALTS

[75] Inventor: Stewart M. Miller, Watchung, N.J.

[73] Assignee: Merck & Co., Inc., Rahway, N.J.

[21] Appl. No.: 753,242

[22] Filed: Dec. 22, 1976

[51] Int. Cl.$^2$ .......................................... C07D 453/04
[52] U.S. Cl. ...................................... 546/135; 546/242
[58] Field of Search .................... 260/DIG. 8, 293.86, 260/284; 546/135

[56] References Cited

U.S. PATENT DOCUMENTS

| 2,528,267 | 10/1950 | Dearborn et al. | 260/570.8 R |
|---|---|---|---|
| 2,742,500 | 4/1956 | Gregory et al. | 260/DIG. 8 |
| 3,705,900 | 12/1972 | Ryan | 260/347.4 |
| 3,959,248 | 5/1976 | Veber et al. | 260/112.5 TR |

OTHER PUBLICATIONS

Eliel, E., *Stereochemistry of Carbon Compounds*, McGraw Hill, New York, 1962, pp. 50–52.
Shabica, A. et al., *J. Am. Chem. Soc.*, 71, 3251 (1949).
Seidell, A., *Solubilities of Organic Compounds*, 3rd ed., vol. II, Van Nostrand, New York, 1941, p. 804.
Chemical Abstracts, 50, 2120f (1956) [Chatten, L., J. Pharm. and Pharmacol. 7, 586–590 (1955)].
*Merck Index*, 9th Ed., Merck and Co., Inc., Rahway, N. J. 1976, pp. 8–9.
Fieser, L., *Organic Experiments*, D.C. Heath, Boston, 1964.
Wiberg, K., *Laboratory Technique in Organic Chemistry*, McGraw Hill, New York, 1960, pp. 110–112.
Dieckmann, W., *Berichte*, 38, 1654–1658 (1905).
Chem. Pharm. Bull., Japan, 19, 1304 (1971).
Greenstein, J., et al., *J. Am. Chem. Soc.*, 75, 1994–1995 (1953).
Allinger, N. et al., Editors, *Topics in Stereochemistry*, vol. 6, Wiley-Interscience, New York, 1971, pp. 132–134.

*Primary Examiner*—Natalie Trousof
*Assistant Examiner*—Richard A. Schwartz
*Attorney, Agent, or Firm*—Daniel T. Szura

[57] ABSTRACT

A process for resolving mixtures of 6-oxo-2-piperidinecarboxylic acid enantiomers using quinine is disclosed.

2 Claims, No Drawings

DEXTRO AND LEVO-6-OXO-2-PIPERIDINECARBOXYLIC ACID QUININE SALTS

BACKGROUND OF THE INVENTION

The present invention involves a process for direct resolution of 6-oxo-2-piperidinecarboxylic acid enantiomer mixtures using quinine as the resolving agent to obtain the individual d and l isomers.

The preparation of the d isomer of 6-oxo-2-piperidinecarboxylic acid (piperidone carboxylic acid) is reported in Journal of the American Chemical Society 75, 1994–1995 (1953). The process consists of three steps, namely chloroacetylation of dl α-amino adipic acid enzymatic resolution of the chloroacetyl-dl-α-aminoadipic acid and finally, cyclization of the individual isomer to prepare the cyclic d 6-oxo-2-piperidinecarboxylic acid. In addition to involving three steps, the enzyme resolution step is very difficult and unreliable.

A simpler procedure for obtaining the individual d or l isomer of 6-oxo-2-piperidinecarboxylic acid has been discovered, which is more direct and does not require the difficult enzyme resolution. This simple procedure involves resolution of e.g. d,l-6-oxo-2-piperidine carboxylic acid by salt formation with quinine and recovering the individual enantiomer from the diastereo isomer salt directly.

SUMMARY OF THE INVENTION

Direct resolution of 6-oxo-2-piperidinecarboxylic acid enantiomer mixture using quinine as the resolving agent.

DESCRIPTION OF THE PREFERRED EMBODIMENTS

An embodiment of this invention is a process for resolving a mixture of 6-oxo-2-piperidinecarboxylic acid enantiomers which comprises
 (a) treating said mixture with quinine in a liquid reaction medium,
 (b) separating the d or l diastereoisomer salts formed by selective crystallization and
 (c) recovering the individual enantiomer from said diastereoisomer salt 6-Oxo-2-piperidinecarboxylic acid, also referred to as homopyrrolidone carboxylic acid (HPCA), has the formula

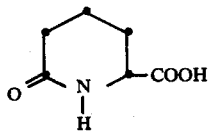

I.

The mixtures of enantiomers of the Formula I compound include physical mixtures of the d- and l-isomers (enantiomers) as well as the d,l racemate.

The resolution is ordinarily carried out in a liquid reaction medium which is a solvent for the quinine and Formula I acid. Acetonitrile and aqueous acetonitrile are preferred liquid reaction media and solvents. Step (a) above is preferably carried out in the substantially anhydrous acetonitrile.

In carrying out the resolution, about 1 mole of quinine is provided per mole of enantiomer mixture. Lesser or greater amounts of quinine may be used, if desired.

The reaction of the enantiomer mixture and quinine is conventionally carried out at about or slightly above room temperature.

The diastereoisomer salts may be separated by direct selective crystallization of the d-acid quinine and l-acid quinine salts. In a more preferred process, the d-acid quinine diastereoisomer is first removed from the d,l diastereoisomer containing, substantially anhydrous solution by seeding with d-6-oxo-2-piperidinecarboxylic acid quinine salt. After thus separating the d-acid quinine salt, the solution contains l-diastereoisomer which is seeded out with l-6-oxo-2-piperidinecarboxylic acid quinine salt, after adding a small amount, up to about 1% by volume of $H_2O$.

The free 6-oxo-2-piperidinecarboxylic acid is obtained from the quinine salt by conventional neutralization with a suitable base.

The l-oxopiperidinecarboxylic acid is useful as a component in certain tripeptides disclosed in U.S. Pat. No. 3,959,248. While the d-oxo-2-piperidinecarboxylic acid may also be useful in preparing such tripeptides, it may also be racemized and the racemate returned for resolution to obtain additional l-isomer.

The l-6-oxo-2-piperidinecarboxylic acid quinine salt and d-6-oxo-2-piperidinecarboxylic acid salt are also embodiments of the present invention.

The following example illustrates the process of the present invention. All temperatures are in °C. unless otherwise indicated. The acetonitrile used in step A is substantially anhydrous.

EXAMPLE 1

Resolution of d,l-6-oxo-2-piperidinecarboxylic acid (HPCA)

A. Preparation of d-HPCA Quinine Salt

Dissolve 2.27 g of anhydrous quinine in 208 ml of acetonitrile with warming and add a suspension of 1 g of dl-HPCA in 180 ml of warm acetonitrile. Seed with the quinine salt of d-HPCA and allow to crystallize at room temperature. When crystallization is complete, filter and wash with two 5-ml portions of acetonitrile and air dry the precipitate. The yield is 1.71 g, mp 213.5°–215.5° dec.

B. Preparation of l-HPCA Quinine Salt

Concentrate the combined mother liquors and wash from the previous step to 25 ml, add 0.25 ml of water and seed with the quinine salt of l-HPCA. Allow to crystallize at room temperature. Filter and wash with two 3-ml portions of acetonitrile and air dry the precipitate. The yield is 1.19 g of solvated product. mp 180°–183°.

To purify, disperse 1 g in 67 ml of acetonitrile containing 1% water warmed to 39° and filter the solution from a trace of insoluble material. Concentrate the filtrate to 11.5 ml, seed with l-HPCA quinine salt and allow to crystallize at room temperature. Filter and wash with three 2-ml portions of acetonitrile and air dry the precipitate. The yield is 0.8759. Mp 159°–160°, resolidifying and remelting at 182°–184°. The material may be desolvated by heating in vacuo at 100°. The rotation (dry basis) $[\alpha]_D^{21} = -140.2°$, C = 2 in 6N HCl.

C. Preparation of l-HPCA

Dissolve a 0.6495 g sample of l-HPCA quinine salt in 19.5 ml of water and make alkaline with 1 ml of 2.5N NaOH. Filter the precipitated quinine after it becomes granular. Acidify the filtrate with 0.85 ml of 2.5N HCl and evaporate to a residue. Extract the residue with anhydrous ethanol and concentrate the extract to a residue. Dissolve the residue in a small amount of water and allow the l-HPCA to crystallize. Filter and wash with water, and vacuum dry at room temperature. The yield is 0.1306 g of partially solvated material. $[\alpha]_D^{21}$ = +35.3°, C = 2 in 6N HCl; or +39.0° corrected for solvation.

E. Preparation of d-HPCA

The reversal of the d-HPCA quinine salt is carried out in the same manner as the l-salt.

Claims to the invention follow.

What is claimed is:
1. l-6-oxo-2-piperidinecarboxylic acid quinine salt.
2. d-6-oxo-2-piperidinecarboxylic acid quinine salt.

* * * * *